(12) United States Patent
Ahn et al.

(10) Patent No.: US 8,554,492 B2
(45) Date of Patent: Oct. 8, 2013

(54) METHOD AND APPARATUS FOR SEARCHING NUCLEIC ACID SEQUENCE

(75) Inventors: Tae-jin Ahn, Seoul (KR); Kyu-Sang Lee, Ulsan (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 181 days.

(21) Appl. No.: 13/074,860

(22) Filed: Mar. 29, 2011

(65) Prior Publication Data

US 2011/0295858 A1 Dec. 1, 2011

(30) Foreign Application Priority Data

May 26, 2010 (KR) ........................ 10-2010-0049117

(51) Int. Cl.
*G06F 19/00* (2011.01)
*G06F 15/00* (2006.01)
*G11C 17/00* (2006.01)
*C12Q 1/68* (2006.01)

(52) U.S. Cl.
USPC ..................... 702/20; 365/94; 700/1; 435/6.1

(58) Field of Classification Search
None
See application file for complete search history.

(56) References Cited

U.S. PATENT DOCUMENTS

| 5,706,498 A | 1/1998 | Fujimiya et al. |
| 2009/0292699 A1 | 11/2009 | Knowles et al. |
| 2009/0307218 A1 | 12/2009 | Selly |

FOREIGN PATENT DOCUMENTS

| JP | 2004-234297 A | 8/2004 |
| KR | 1020020075852 A | 10/2002 |
| KR | 1020040070438 A | 8/2004 |
| KR | 1020060002792 A | 1/2006 |

OTHER PUBLICATIONS

Brandon et al. Data structures and compression algorithms for genomic sequence data Bioinformatics vol. 25, pp. 1731-1738 (2009).*

* cited by examiner

*Primary Examiner* — John S Brusca
(74) *Attorney, Agent, or Firm* — Leydig, Voit & Mayer, Ltd.

(57) ABSTRACT

A method and apparatus for searching compressed nucleic acid sequences are disclosed. In the method, a reference sequence is compared with a subject sequence to be encoded, the subject sequence is compressed, an index is created with respect to the reference sequence and the compressed subject sequence, a position corresponding to a query is searched for in the compressed subject sequence using the index, a character found at the position within the compressed sequence is converted into a sequence, and the sequence is output as the response to the query.

21 Claims, 11 Drawing Sheets

FIG. 3A

```
            305                                                     305
             ↓                                                       ↓
   1 2 3 4 5 6 7 8 9 10 11 12 13 14 15 16 17 18 19 20 21 22 23 24 25 26 27 28 29 30 31 32 33 34 35 36 37 38 39 40 41 42 43 44 45 46 47
Reference
   G C T T G A C T A A T G C A A G T A G A A A A A A - A C A A A T A A G T G T T A T G A A T C C C        ←301 (SEQ ID NO:1)
   | | | | | | | | | | | | | | | | | | | | |   | | | | | | | | | | | | | | | | | |   | | |
Personal
Genome
   G C T T G A C T A A T G C A A G T A G A A A A A A T A - A A A T A A G T G T T A T G A A T C C C        ←302 (SEQ ID NO:2)
```

Encoded Personal Genome              L L L L L L L L L L L L L L L L L L L L L T L X L L L L L L L L L L L L L L L L L L L L L L L L L        ←303

Modified Encoded Personal            L 2 0 L 4 T L X L 1 4 L 6                    L 2 4 T L X L 2 0        ←304
Genome for indexing                        ↑                                             ↑
                                          21                                            41
                                           ↓                                             ↓
Index pointing position at                306                                           306
reference sequence

FIG. 7

```
   1 2 3 4 5 6 7 8 9 10 11 12 13 14 15 16 17 18 19 20 21 22 23 24 25 26 27 28 29 30 31 32 33 34 35 36 37 38 39 40 41 42 43 44 45 46
   L L L L L L L L L  L  L  L  L  L  L  L  L  L  L  L  L  L  L  L  L  L  X  L  L  L  L  L  L  L  L  L  L  L  L  L  L  L  L  L  L  L
   G C T T G A C T A A  T  G  C  A  A  G  T  A  G  A  A  A  A  A  -  A  C  A  A  A  A  T  A  A  G  T  G  T  T  A  T  G  A  A  T  C    (SEQ ID NO:1)
   | | | | | | | | |    |  |  |  |  |  |  |  |  |  |  |  |  |  |     —  —  |  |  |  |  |  |  |  |  |  |  |  |  |  |  |  |  |  |
   G C T T G A C T A A  T  G  C  A  A  G  T  A  G  A  A  A  A  A  A  T  A  -  A  A  A  A  T  A  A  G  T  G  T  T  A  T  G  A  A  T  C  (SEQ ID NO:2)
```

701

METHOD AND APPARATUS FOR SEARCHING NUCLEIC ACID SEQUENCE

CROSS-REFERENCE TO RELATED APPLICATIONS

This application claims the benefit of Korean Patent Application No. 10-2010-0049117, filed on May 26, 2010, and all the benefits accruing therefrom under 35 U.S.C. §119, the disclosure of which is incorporated herein in its entirety by reference.

BACKGROUND

1. Field

The present disclosure relates to methods and apparatuses for searching a nucleic acid sequence.

2. Description of the Related Art

With the development of biotechnology, deoxyribonucleic acid (DNA) sequences that contain specific genetic information of an organism have been determined and analyzed. Such DNA sequence analysis may be used for various purposes, such as finding genetic factors that cause phenotypic variations and diseases of organisms, and is actively performed with the aid of a computer. In this regard, a nucleic acid sequence is converted into a computer readable form. However, since a nucleic acid sequence contains bulky genetic information and the need for storage of DNA sequences is increasing, enormous costs for nucleic acid sequence storage and transfer is incurred. Therefore, in order to reduce the cost for its storage and transfer, compression of the nucleic acid sequence is required. When a customized diagnosis is performed on an organism by using DNA sequence analysis, it is necessary to obtain nucleic acid information regarding a portion of the genome related to a disease or heredity from the compressed DNA sequence of an organism. To date, desired nucleic acid information may be searched for and obtained only by restoring a compressed nucleic acid sequence back to the original nucleic acid sequence. Thus, there is a need for a method of efficiently searching compressed nucleic acid sequence for desired nucleic acid information.

SUMMARY

Provided are methods and apparatuses for searching a nucleic acid sequence. In an embodiment, the nucleic acid is deoxyribonucleic acid (DNA).

Additional aspects will be set forth in part in the description which follows and, in part, will be apparent from the description, or may be learned by practice of the presented embodiments.

According to an aspect of the present invention, a method of searching a nucleic acid sequence includes comparing a reference sequence having known nucleic acid information with a subject sequence to be encoded, converting the subject sequence into a string of characters, according to a conversion rule, and compressing the subject sequence by using the converted string of characters; setting an index position of a corresponding position of the reference sequence and the compressed subject sequence, and creating an index; when a query regarding nucleic acid information of the subject sequence is input, searching for a position corresponding to the query in the converted string of characters by using the created index; and converting a character of the found characters into a sequence according to the conversion rule, and outputting the character as a response to the query.

According to another aspect of the present invention, a method of searching a nucleic acid sequence from a subject sequence that is converted from a reference sequence having known nucleic acid information into a string of characters includes setting an index position of a corresponding position of the reference sequence and the compressed subject sequence, and creating an index; when a query regarding nucleic acid information of the subject sequence is input, searching for a position corresponding to the query in the converted string of characters by using the created index; and converting a character of the found characters into a sequence according to the conversion rule, and outputting the character as a response to the query.

According to another aspect of the present invention, a computer readable recording medium has recorded thereon a program for executing a method of searching a nucleic acid sequence.

According to another aspect of the present invention, an apparatus for searching a nucleic acid sequence includes a compression unit for comparing a reference sequence having known nucleic acid information with a subject sequence to be encoded, converting the subject sequence into a string of characters, according to a conversion rule, and compressing the subject sequence by using the converted string of characters; an index unit for setting an index position of a corresponding position of the reference sequence and the compressed subject sequence, and creating an index; a searching unit, when a query regarding DNA information of the subject sequence is input, for searching for a position corresponding to the query in the converted string of characters by using the created index; and a sequence converting unit for converting a character of the found character into a sequence according to the conversion rule, and outputting the character as a response to the query.

According to another aspect of the present invention, an apparatus for searching a nucleic acid sequence from a subject sequence that is converted from a reference sequence having known nucleic acid information into a string of characters includes an index unit for setting an index position of a corresponding position of the reference sequence and the compressed subject sequence, and creating an index; a searching unit, when a query regarding nucleic acid information of the subject sequence is input, searching for a position corresponding to the query in the converted string of characters by using the created index; and a sequence converting unit for converting a character of the found character into a sequence according to the conversion rule, and outputting the character as a response to the query.

BRIEF DESCRIPTION OF THE DRAWINGS

These and/or other aspects will become apparent and more readily appreciated from the following description of the embodiments, taken in conjunction with the accompanying drawings of which:

FIG. 3A is a diagram illustrating the process of creating an index, according to an embodiment of the present invention;

FIG. 7 is a diagram illustrating the a process of converting a sequence according to a search result in a sequence converting unit, according to an embodiment of the present invention;

DETAILED DESCRIPTION

Reference will now be made in detail to embodiments, examples of which are illustrated in the accompanying drawings.

Figure 1:
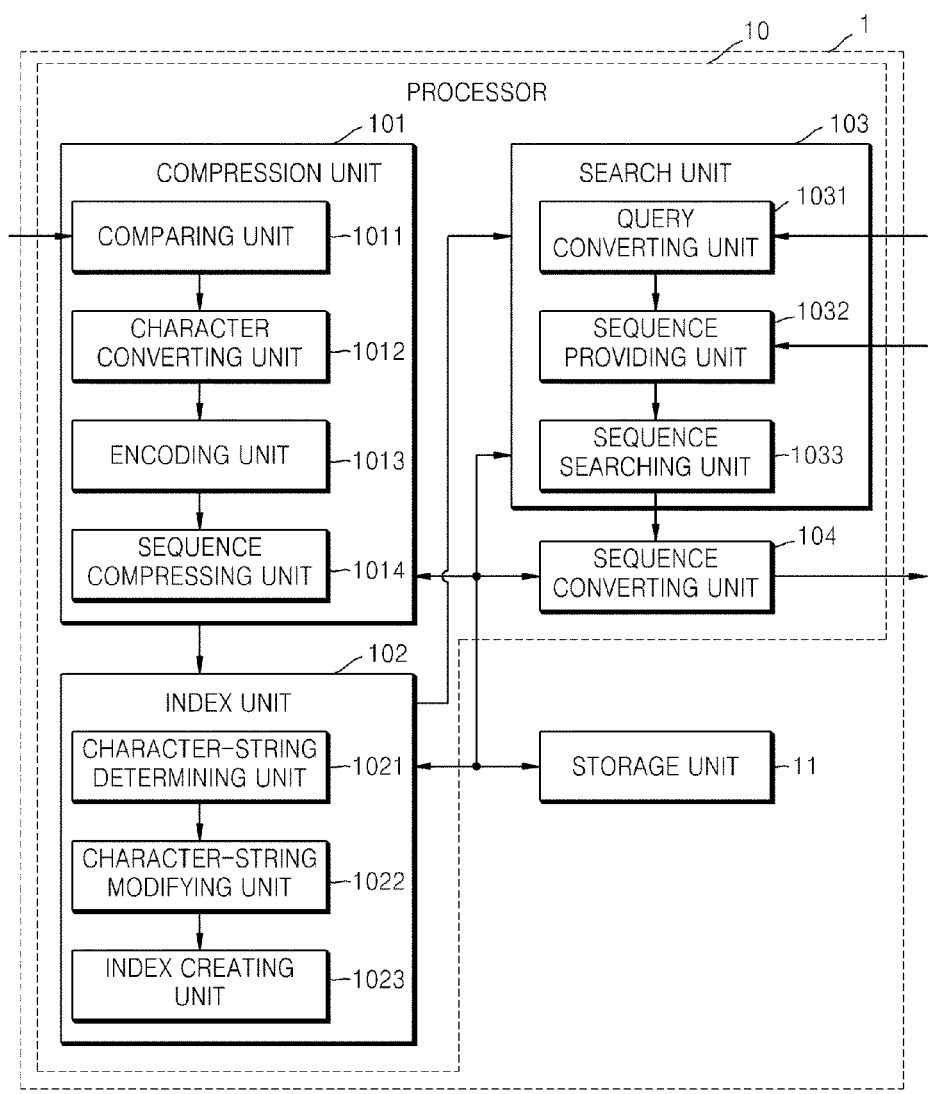
FIG. 1 is a structural diagram of a nucleic acid sequence searching apparatus according to an embodiment of the present invention.

FIG. 1 is a structural diagram of a nucleic acid sequence searching apparatus 1 according to an embodiment of the present invention. The nucleic acid sequence can be a DNA or RNA sequence. Referring to FIG. 1, the nucleic acid sequence searching apparatus 1 includes a processor 10 and a storage unit 11. The processor 10 includes a compression unit 101, an index unit 102, a searching unit 103, and a sequence converting unit 104. The processor 10 may be configured in an array including a plurality of logic gates, or may be configured with a combination of a general-purpose microprocessor and a memory that is executed in the general-purpose microprocessor. In addition, it will be understood by one of ordinary skill in the art that the processor 10 may be configured in other hardware forms. In order not to diminish the clarity of the points of the embodiments of the present invention, only hardware components related to embodiments of the present invention will be described through the specification. However, it will be understood by one of ordinary skill in the art that the processor 1 may include other hardware components, in addition to hardware components shown in FIG. 1.

DNA of an organism refers to the genetic material containing genetic information of the organism. DNA is represented by a DNA sequence including four bases. The DNA sequence contains information of cells and tissues constituting the organism. The bases of the DNA sequence in genes provides information regarding the connection or arrangement sequence of twenty amino acids as components of a protein query of the organism. Thus, a specific genetic phenotype is realized by the DNA sequence as a gene, according to information indicated by the bases contained in the DNA sequence.

Recently, the complete genome of humans has been revealed through the human genome project. Research on the genome DNA sequence of humans and other organisms has been conducted in various fields, such as diagnosis and disease prevention, or biological inheritance of organisms. In this research, since a computer analyzes a large amount of information, the new field of bioinformatics has been introduced. Bioinformatics refers to the field of processing information, such as a DNA sequence, to obtain genetic information or disease information. Thus, bioinformatics includes any field of studying biology with a computer. For example, bioinformatics includes various fields of determining a function of a protein query from a DNA sequence, or determining a structure of the protein query and predicting the function of the protein query.

In one aspect, a single nucleotide polymorphism (SNP) of an organism's genome may be determined by analyzing the DNA sequence. A SNP refers to a type of single nucleotide variation within the same species of organism. When a SNP occurs in a coding region of the DNA sequence, a defective or altered protein may be expressed, causing disease. Thus, if defects or altered portions of the DNA sequence are discovered and corrected, a disease may be correctly treated, or if a disease is discovered and treated prior to discovery of the disease, the disease may be prevented.

However, since a human's DNA sequence contains bulky genetic information, enormous cost for storing many human DNA sequences and processing the stored DNA sequences is incurred, in order to analyze a DNA sequence with a computer. Thus, there is a need for a lossless data compression technology compressing a nucleic acid sequence, particularly a DNA sequence, while maintaining information of a particular sequence. Also there is a need for a technology of correctly searching for and analyzing a SNP in the compressed DNA sequence.

The nucleic acid sequence searching apparatus 1 according to an embodiment of the invention may efficiently compress and store a DNA sequence. Then, the nucleic acid sequence searching apparatus 1 may correctly search the compressed DNA sequence for a base sequence of a position desired by a user and analyze the base sequence without the need to restore the compressed DNA sequence back to the original DNA sequence, for analysis of the DNA sequence. Hereinafter, a configuration and an operation of the nucleic acid sequence searching apparatus 1 will be described. For convenience, the description will emphasize operations on DNA sequence information, but the apparatus can be configured and operated with other nucleic acid sequence information, e.g., RNA sequences.

The compression unit 101 compares a reference sequence having known DNA information with a subject sequence to be encoded, converts the subject sequence into a string of characters, according to a conversion rule, and compresses the subject sequence by using the string of characters. The compression unit 101 includes a comparing unit 1011, a character converting unit 1012, an encoding unit 1013, and a sequence compressing unit 1014.

The comparing unit 1011 aligns and compares the subject sequence to be encoded with the reference sequence having known DNA information. In this case, the subject sequence and the reference sequence are aligned so that the subject sequence and the reference sequence are matched as much as possible. The comparing unit 1011 extracts the consistency and difference between the reference sequence and the subject sequence, as a comparison result. The reference sequence and the subject sequence are compared using a known algorithm for sequence comparison, e.g., a basic local alignment search tool (BLAST), BLAST-like alignment tools (BLAT), the FASTA algorithm, or the smith waterman algorithm. The comparison result may be output in a document format such as text, html, or xml. In addition, the consistency and difference between the reference sequence and the subject sequence may be extracted from the comparison result by using a known parsing method.

The character converting unit 1012 converts information of the extracted consistency and difference between the reference sequence and the subject sequence into a string of characters, according to a conversion rule. In addition, the encoding unit 1013 encodes individual characters constituting the string of characters by using conversion codes corresponding to the individual characters.

The sequence compressing unit 1014 compresses the subject sequence by using the encoded result based on the conversion codes from the string of characters. The sequence compressing unit 1014 compresses the encoded result by using a general compression method. A compression algorithm that may be used herein may be a tool known in the data compression field, such as LZ78, Hoffman coding, and computing coding. Furthermore, various known compression technologies related to compression of genetic information may be used.

The conversion rule and the conversion codes are defined in Table 1, and it will be understood by one of ordinary skill in the art that other rules and codes may also be used.

TABLE 1

| 4 bit | | | 8 bit | | |
|---|---|---|---|---|---|
| bit | Hexadecimal (Decimal) | Meaning | bit | Hexadecimal (Decimal) | Meaning |
| 0000 | 0(0) | 0 | 1111 0000 | F0(240) | X (deletion) |
| 0001 | 1(1) | 1 | 1111 0001 | F1(241) | R |
| 0010 | 2(2) | 2 | 1111 0010 | F2(242) | Y |
| 0011 | 3(3) | 3 | 1111 0011 | F3(243) | S |
| 0100 | 4(4) | 4 | 1111 0100 | F4(244) | W |
| 0101 | 5(5) | 5 | 1111 0101 | F5(245) | K |
| 0110 | 6(6) | 6 | 1111 0110 | F6(246) | M |
| 0111 | 7(7) | 7 | 1111 0111 | F7(247) | B |
| 1000 | 8(8) | 8 | 1111 1000 | F8(248) | D |
| 1001 | 9(9) | 9 | 1111 1001 | F9(249) | H |
| 1010 | A(10) | A | 1111 1010 | FA(250) | V |
| 1011 | B(11) | C | 1111 1011 | FB(251) | N |
| 1100 | C(12) | G | 1111 1100 | FC(252) | . or - |
| 1101 | D(13) | T | 1111 1101 | FD(253) | (null) |
| 1110 | E(14) | L (the same as reference sequence) | 1111 1110 | FE(254) | (null) |
| 1111 | F(15) | Read subsequent 4-bit codes | 1111 1111 | FF(255) | EOF |

As shown in Table 1, according to the comparison result of the comparing unit 1011, the character converting unit 1012 converts the consistency between the reference sequence and the subject sequence into a character "L", and converts the difference between the reference sequence and the subject sequence by using different characters such as A, C, G, T, and the like. In addition, when the same characters are repeatedly marked, the same characters are converted by using the repeating number of characters. In Table 1, meanings corresponding to hexadecimal numbers are made with reference to the DNA codes of the International Union Of Pure And Applied Chemistry (IUPAC). According to the present embodiment, since all sequence codes of the IUPAC may be marked according to Table 1, a DNA sequence may be compressed by using the IUPAC sequence codes. That is, even if a DNA sequence is represented not by characters, such as A, C, T and G, corresponding to the four bases, but by an IUPAC Ambiguity Code, the DNA sequence may be compressed. For example, when a DNA sequence at a predetermined position may correspond to A or G, e.g., if a human's gene sequence is composed of the sequences on a pair of chromosomes that are inherited from the human's father and mother, respectively, the two bases to 'A' and 'G' may be represented by the single IUPAC ambiguity code 'R'. Thus, for marking the chromosomes on the DNA sequence, the IUPAC code 'R' is marked. If such characters may not be marked in a compression method, information of a human's gene may not be compressed.

The encoding unit 1013 encodes individual characteristics of the string of characters including the converted characters by corresponding 4-bit or 8-bit conversion codes of Table 1. That is, the conversion rule indicates that characters are assigned to the consistency, the difference and the number of characters in the consistency or difference between the reference sequence and the subject sequence. In addition, the conversion code indicates that 4-bit and 8-bit codes are assigned to the assigned characters.

For example, when the characters converted by the character converting unit 1012 are L24TLF0L20, the encoding unit 1013 encodes the converted characters into '1110 0010 0100 1101 1110 1111 0000 1110 0010 0000'. As such, by encoding the DNA sequence into the conversion codes, the subject sequence may be encoded without loss of DNA information. The sequence compressing unit 1014 compresses the encoded result. Thus, when subject sequences of organisms are compressed based on a reference sequence having known DNA information, the DNA information of the subject sequences may be stored by storing only the compressed encoded codes from a single reference sequence and the subject sequences without using the original subject sequences of the organisms.

Figure 2:
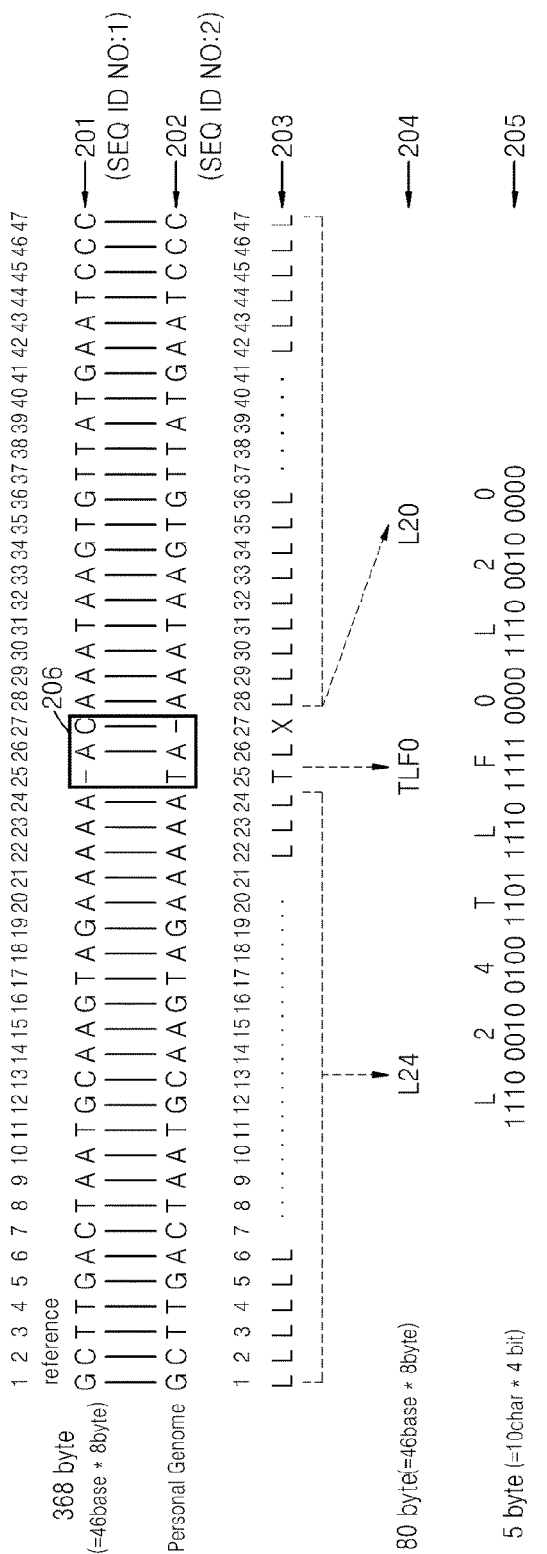
FIG. 2 is a diagram illustrating an example in which a compression unit compresses a subject sequence, according to an embodiment of the present invention.

FIG. 2 is a diagram illustrating a case in which the compression unit 101 compresses a subject sequence, according to an embodiment of the present invention. Referring to FIG. 2, a reference sequence 201 (SEQ ID NO: 1), a subject sequence 202 (SEQ ID NO: 2), a consistency and difference 203, a converted string of characters 204, and encoded codes 205 are illustrated.

First, the comparing unit 1011 compares the reference sequence 201 with the subject sequence 202 to extract a difference 206 between the reference sequence 201 and the subject sequence 202, and a consistency between the reference sequence 201 and the subject sequence 202.

The character converting unit 1012 converts the consistency into a character 'L', and converts the difference 206 into the characters 'TLF0' corresponding to the difference 206 with reference to Table 1. Numbers '24' and '20' of L24 and L20 of the converted string of characters 204 indicate the number of repeating 'L's. For this example, with respect to the characters 'TLF0' of the converted string of characters 204, since a base 'T' is marked as being only in the subject sequence at a starting point of the difference 206, the base 'T' is converted into the character 'T'. Since the central subsequence bases of the difference 206 are the same, the consistency is converted into a character 'L'. In addition, the subsequent base 'C' is marked as being only in the reference sequence, and is deleted on the subject sequence. Thus, the difference is converted into the character 'F0', representing a deletion (X).

Then, the encoding unit 1013 encodes 'L24TLF0L20' of the converted string of characters 204 by using the conversion code of Table 1. With reference to Table 1, 'L' corresponds to '1110' of 4-bit codes, '2', '4' and '0' correspond to '0010', '0100' and '0000', respectively, 'T' corresponds to '1101', and F0 corresponds to '1111 0000'. Thus, as the encoding result, L24TLF0L20 is encoded into '1110 0010 0100 1101 1110 1111 0000 1110 0010 0000' (line 205 of FIG. 2).

FIG. 2 illustrates an example of a relatively short DNA sequence consisting of 368 bytes. The subject sequence of 368 bytes is converted into a string of characters of 80 bytes (line 204), and then is encoded into codes of 5 bytes (line 205). Thus, the compression unit 101 may efficiently compress an original DNA sequence without a loss of DNA information. Although a DNA sequence of an organism such as a human contains a larger amount of DNA information than in the above-described example, the compression unit 101 may also efficiently compress a larger DNA sequence without loss of DNA information by using the above-described method.

Referring back to FIG. 1, the storage unit 11 may store the reference sequence that is processed by the compression unit 101, the converted string of characters, and the encoded codes, and may be used to read out, search for, and analyze the subject sequence, if necessary.

According to the present embodiment, the compression unit 101 may further include a pre-processor (not shown). The pre-processor may pre-process the reference sequence, and such pre-process may also be referred to as an encryption process.

First, the pre-processor creates a variation sequence generation function for the reference sequence. The variation sequence generation function is a function that uses, as inputs, random variables that may be obtained by a technique embodied in computing science, for example, a random number generation algorithm. The pre-processor modifies the reference sequence by using a variation sequence generation factor selected from among created variation sequence generation factors obtained based on the variation sequence generation function. The modified reference sequence is stored in the storage unit 11. In this case, the reference sequence and the selected variation sequence induction factors are separately stored as secret keys. Thus, when the reference sequence is encoded after modified by the pre-processor, the security of a DNA sequence is enhanced.

A user may determine a SNP by analyzing the DNA information of the base sequence of a predetermined position, which is obtained from a subject sequence. Typically, when a subject sequence is compressed, in order to obtain DNA information of a base sequence of a predetermined position, the compressed subject sequence needs to be restored to the original DNA sequence, and then the DNA information of the base sequence of a predetermined position may be obtained from the restored DNA sequence. However, an enormous amount of computer time for restoration and search of the original DNA sequence is required due to the bulky nature of genetic information.

However, the nucleic acid sequence searching apparatus 1 according to the present embodiment may create and store an index of a compressed subject sequence, and may subsequently search the compressed subject sequence by using the stored index without restoring the compressed subject sequence to its original form. Thus, the DNA sequence searching apparatus 1 may efficiently search a DNA sequence. Hereinafter, the operation of index unit 102 in creating an index of a compressed subject sequence will be described, and then the operation of the searching unit 103 for searching the compressed subject sequence by using the index will be described.

The index unit 102 sets an index position at a corresponding position of the reference sequence and of the compressed subject sequence, and creates an index based on the index position. The index created by the index unit 102 is created by mapping the set index position of the reference sequence with a position of a character corresponding to the index position in the converted string of characters. Alternatively, the index may be created by mapping the index position of the reference sequence with a position of a code corresponding to the index position in the encoded codes.

Index positions are set in predetermined positions of the reference sequence, based on the reference sequence. The index positions may be set by predetermined intervals, or may be set in predetermined positions according to a user's settings. For example, when the index positions are set at predetermined intervals, the index positions are set with respect to positions of 100 units of bases from a starting position of the reference sequence.

The index unit 102 includes a character-string determining unit 1021, a character-string modifying unit 1022, and an index creating unit 1023.

The character-string determining unit 1021 may determine whether a converted character that is converted according to the conversion rule exists in a converted string of characters in the position of the subject sequence corresponding to the index position. In addition, the character-string determining unit 1021 may directly determine whether the converted character exists in the encoded codes. For example, if the first to the $25^{th}$ bases of a reference sequence are the same as those of a subject sequence, the subject DNA sequence is converted into a string of characters 'L25'. In this case, if the index position of the reference sequence is set as the $21^{st}$ base, only the number is marked, but the $21^{st}$ base is not shown. Thus, the character-string determining unit 1021 determines that a character corresponding to the index position does not exist in the converted string of characters. This is also applied for the determination based on encoded codes.

When the character-string determining unit 1021 determines that the character corresponding to the index position does not exist in the converted string of characters, the character-string modifying unit 1022 modifies the converted string of characters so that a character that is converted in a position of the subject sequence corresponding to the index position may be expressed in a string of characters. That is, with reference to the above-described example, the character-string modifying unit 1022 modifies the string of characters 'L25' to 'L20L5' so that a character 'L' corresponding to the index position $21^{st}$ may be expressed, and then creates an index. If the character corresponding to the index position is expressed, the index is directly created. This is also applied for the determination based on encoded codes.

The index creating unit 1023 maps the index position with the position of the character corresponding to the index position in the converted string of characters, and creates an index. A process of creating the index will be described in more detail, with reference to FIGS. 3A, 3B, and 3C.

FIG. 3A is a diagram illustrating the process of creating an index, according to an embodiment of the present invention.

The sequences in FIG. 3A are identical to the reference sequence and subject sequence of FIG. 2. Referring to FIG. 3A, index positions 305 are set at the 21$^{st}$ and 41$^{st}$ base positions of the reference sequence 301 (SEQ ID NO: 1), aligned with the subject sequence 302 (SEQ ID NO: 2). The converted string of characters 303 for the encoded subject sequence is shown. The subject sequence 302 (SEQ ID NO: 2) is converted into a converted string of characters 303, that is, L24TLXL20. All characters that are converted in positions of the subject sequence 302 (SEQ ID NO: 2) corresponding to the subject sequence 302 (SEQ ID NO: 2) of the reference sequence 301 (SEQ ID NO: 1) may be 'L'. However, since the 21$^{st}$ and 41$^{st}$ positions of the subject sequence 302 (SEQ ID NO: 2) are not shown explicitly in the converted string of characters 303, the character-string modifying unit 1022 modifies the converted string of characters 303 to a new string of characters 304, "L20L4TLXL14L6". The character 'L' 306 corresponding to each of the index positions 305 of reference sequence 301 (SEQ ID NO: 1) is marked in the modified string of characters 304. That is, the index creating unit 1023 maps the index positions 305 with the position of the character 'L' 306 of the modified converted string of characters 304 to create an index. Thus, the 21$^{st}$ base of the reference sequence 301 (SEQ ID NO: 1) of the index positions 305 is mapped with the fourth character 'L' of the modified string of characters 304. The 41$^{st}$ base of the reference sequence 301 (SEQ ID NO: 1) is mapped with the 13$^{th}$ character 'L' of the modified string of characters 304 since a character 'X' is encoded into an 8-bit code in the modified string of characters 304, unlike the character 'L'

Figure 3B:
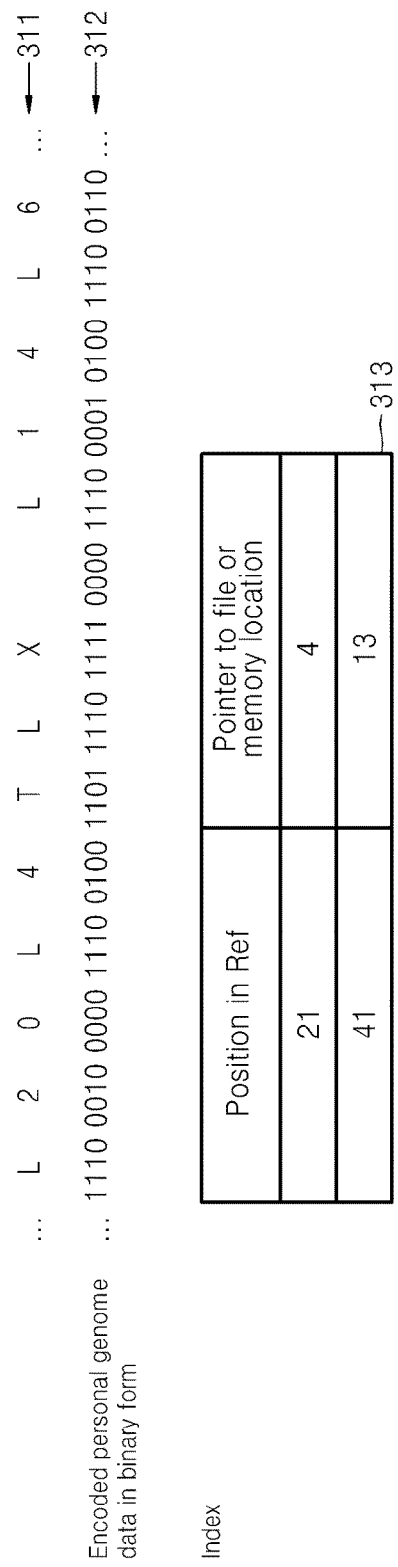
FIG. 3B is a diagram illustrating the process of creating the index of FIG. 3A in more detail.

FIG. 3B is a diagram for explaining the process of creating the index of FIG. 3A in more detail. Referring to FIG. 3B, the modified string of characters 311 and corresponding encoded codes 312 based on the conversion code are illustrated. As described above with reference to FIG. 3A, the index positions, that is, the 21$^{st}$ and 41$^{st}$ base positions of the reference sequence, correspond to the fourth and thirteenth characters in the modified string of characters 311. Thus, the index creating unit 1023 maps the index positions to create an index 313. When bases in predetermined positions are searched for in a compressed subject sequence, bases in the desired positions may be rapidly found by using the created index 313.

Figure 3C:
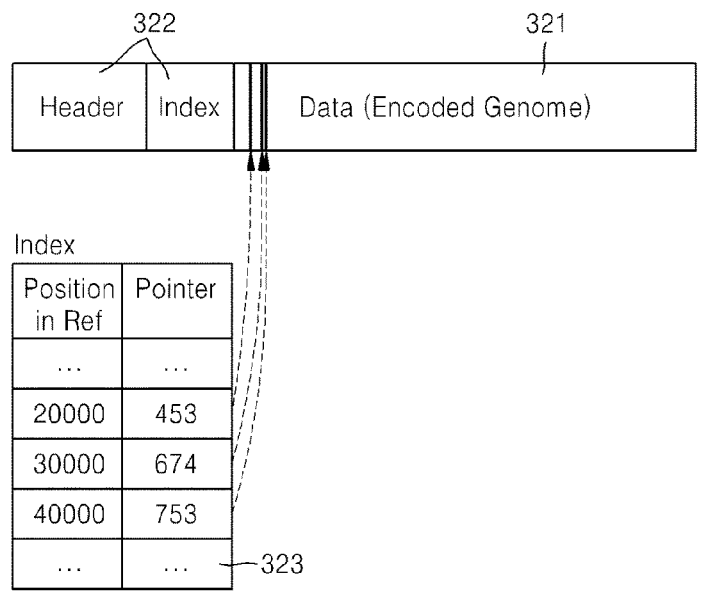
FIG. 3C is a diagram illustrating the process of storing a created index together with a compressed subject sequence, according to an embodiment of the present invention.

FIG. 3C is a diagram for explaining the process of storing a created index together with a compressed subject sequence, according to an embodiment of the present invention. Referring to FIG. 3C, a subject sequence compressed by the compression unit 101 is stored in storage unit 11 in a form generated by mapping the data region 321 where encoded codes are recorded, and the header and index 322 where various additional materials, e.g., information about the reference sequence, are recorded. If the index unit 102 creates a new index 323, the storage unit 11 of FIG. 1 maps and stores the new index 323 in addition to the data 321, the header and index 322, and the created new index 323.

Referring back to FIG. 1, the searching unit 103 searches a sequence according to a user's request. That is, when a query regarding DNA information of a subject sequence is input, the searching unit 103 searches the converted string of characters for a position corresponding to the query, by using the created index. The searching unit 103 searches a desired position starting from an index position positioned prior to the desired position among index positions included in the created index. As such, by searching for the desired position by using the index, since the position corresponding to the query does not have to be searched for from the beginning of the string of characters, the desired position may be efficiently and rapidly found.

The searching unit 103 includes a query converting unit 1031, a sequence providing unit 1032, and a sequence searching unit 1033.

When a query regarding DNA information of a subject sequence is input from a user, the query converting unit 1031 converts the input query into a query indicating the kind of reference sequence, and a position to be searched for in the reference sequence. The query input from the user corresponds to a biological and medical external query. For example, a biological and medical external query corresponds to a query "search for the sequence of the 12$^{th}$ and 13$^{th}$ codons of the KRAS gene." The biological and medical external query needs to be converted into an internal query so as to be read by the searching unit 103. That is, for example, the query "search for the sequence of the 12$^{th}$ and 13$^{th}$ condons of the KRAS gene." is converted into an internal query such as "search for the sequence of Chromosome 12 based on the human reference sequence of NCBI build 36.1" in the query converting unit 1031. To this end, the query converting unit 1031 communicates with a database, stored in an external storage unit or the storage unit 11, in which the gene coordinates of a primary marker are stored. The primary marker can be, for example, a SNP, a copy number variation (CNV), or a mutation. The query converting unit 1031 then converts the external query into an internal query. The converted internal query corresponds to the query to be searched for based on the reference sequence.

The sequence providing unit 1032 provides the reference sequence indicated by the converted internal query. That is, the sequence providing unit 1032 reads-out the reference sequence that is stored in storage unit 11 or an external database (not shown), and provides the reference sequence to the sequence searching unit 1033. In addition, the sequence providing unit 1032 also provides information regarding the compressed subject sequence corresponding to the internal query. That is, the sequence providing unit 1032 provides information in which a header, an index, and encoded data and index are mapped, as represented in FIG. 3C, to the sequence searching unit 1033.

The sequence searching unit 1033 searches for the position corresponding to the query of which a subject sequence is converted into the converted string of characters, in the reference sequence provided by using the created index. In more detail, the sequence searching unit 1033 searches for an index position of the reference sequence, which is the closest to the position indicated by the internal query, by using the index. Then, if the index position is found, the character corresponding to the position indicated by the internal query in the string of characters is searched for based on the index position. After the search is completed, the character of the searched position is transmitted to the sequence converting unit 104. When the character corresponding to the position indicated by the internal query is searched for, the character may be searched for based on the string of characters into which the subject sequence is converted, or alternatively, may be searched for based on codes into which the string of characters are encoded. That is, when the character is searched for based on the encoded codes, the characters may be searched for while shifted by 4-bit or 8 bit codes from the index position.

When the input query is a query regarding a plurality of different subject sequences, the searching unit 103 conducts parallel searches for the subject sequences indicated by the converted query. That is, in order to efficiently process a query, the query is parallely distributed to various sequences, and then the query may be simultaneously searched for with respect to the various sequences.

Figure 4:
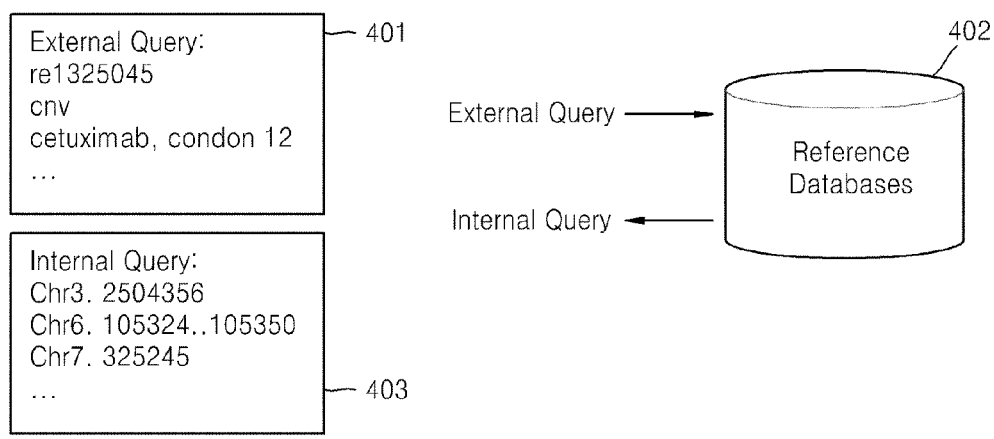
FIG. 4 is a diagram illustrating the process of converting a query in a query converting unit, according to an embodiment of the present invention.

FIG. 4 is a diagram for explaining the process of converting a query in the query converting unit 1031, according to an embodiment of the present invention. Referring to FIG. 4, when an external query 401 is input by a user, the query converting unit 1031 communicates with a database 402 in which gene coordinates of a primary marker are recorded, and then converts the external query 401 into an internal query 403. Database 402 is stored in an external storage unit or in storage unit 11.

Figure 5:
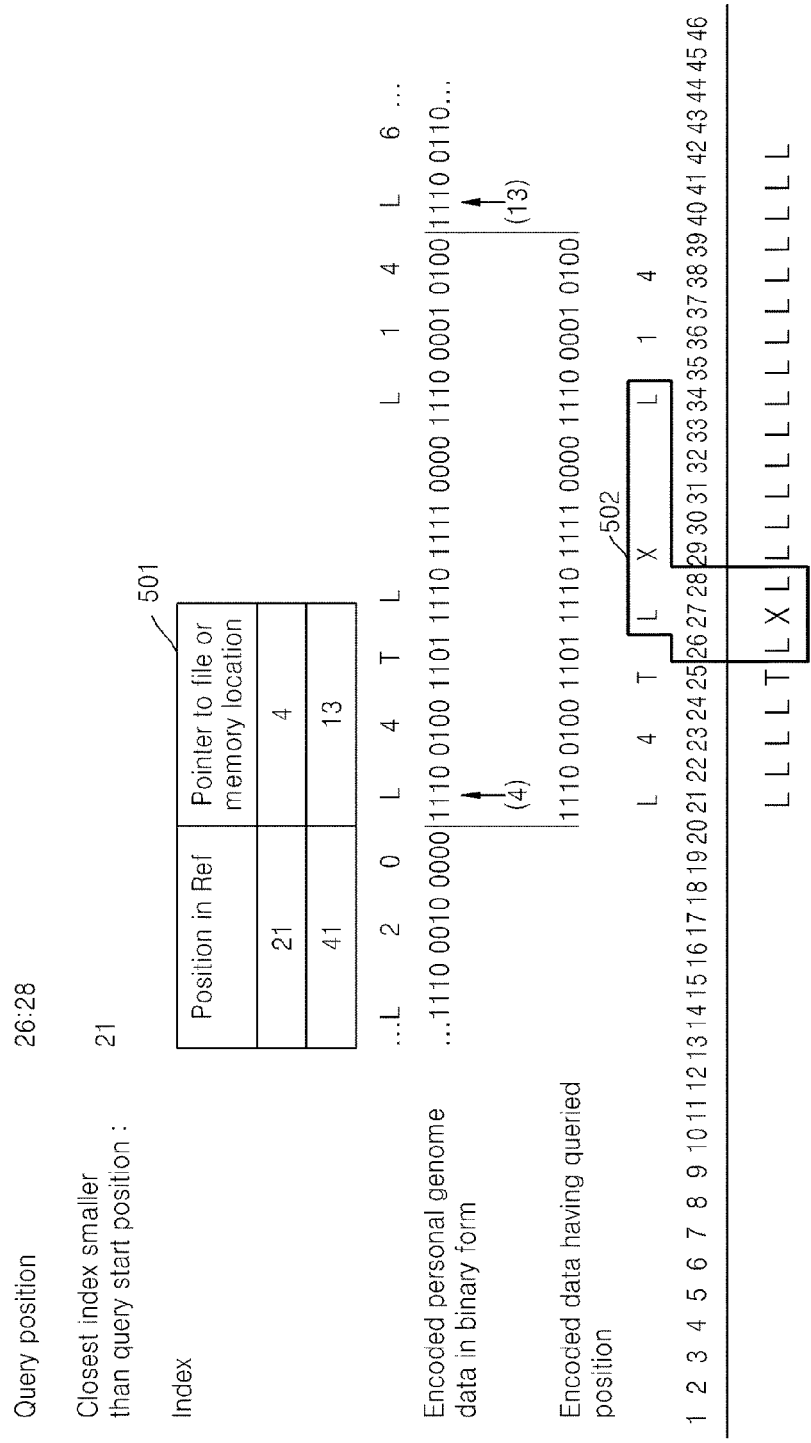
FIG. 5 is a diagram illustrating the a process of searching for a position corresponding to a query in a sequence searching unit, according to an embodiment of the present invention.

FIG. 5 is a diagram for explaining the process in the sequence searching unit 1033 of searching for a position corresponding to a query, according to an embodiment of the present invention. The query converting unit 1031 converts the external query input by the user into an internal query for the $26^{th}$ to $28^{th}$ base sequences of the reference sequence.

As described above, the sequence searching unit 1033 searches for the index position of the reference sequence which is the closest to the position indicated by the internal query. In FIG. 5, the sequence searching unit 1033 searches index 501 for the index position of the reference sequence which is the closest to the position indicated by the internal query, and selects the $21^{st}$ index position. The $21^{st}$ position of the reference sequence in index 501 corresponds to the fourth character or code in the converted string of characters or encoded codes. Since the query is for the $26^{th}$ to $28^{th}$ base sequences, the sequence searching unit 1033 searches for the characters corresponding to the $26^{th}$ to $28^{th}$ base sequences of the reference sequence and the subject sequence. Since the string of characters corresponding to the $26^{th}$ to $28^{th}$ base sequences is 'LXL', the sequence searching unit 1033 outputs 'LXL' as the search result.

Figure 6:
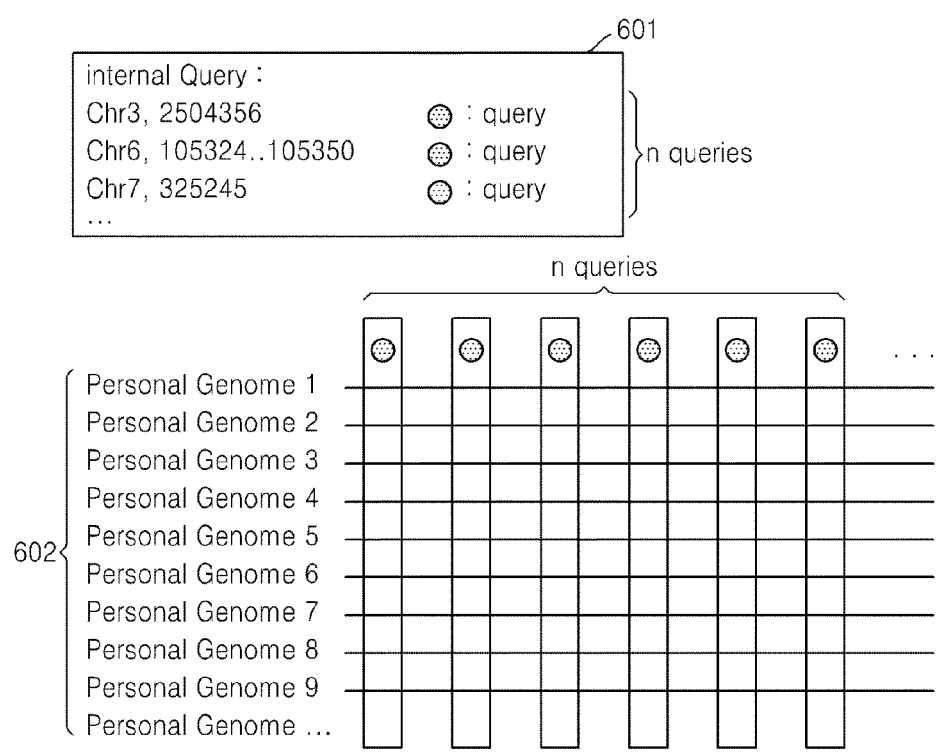
FIG. 6 is a diagram illustrating the process of parallel distributing a query in a sequence searching unit, according to an embodiment of the present invention.

FIG. 6 is a diagram for explaining the process of parallely distributing a query in the sequence searching unit 1033, according to an embodiment of the present invention. Referring to FIG. 6, when a plurality of different queries 601 are input, the different queries 601 may be simultaneously searched for in parallel with respect to the different subject sequences 602.

Referring back to FIG. 1, the sequence converting unit 104 converts the character of the searched position into a sequence according to the conversion rule, and outputs the sequence as a response to the query. In an embodiment, Table 1 may be used as the conversion rule. In FIG. 5, the sequence searching unit 1033 outputs 'LXL', as the search result with respect to the query for the $26^{th}$ to 28 base sequences of the subject sequence, to the sequence converting unit 104. The sequence converting unit 104 converts 'LXL' into the base sequence 'A-A', with respect to the conversion rule of FIG. 1 and the reference sequence. That is, the sequence converting unit 104 outputs to the user the base sequence 'A-A' as the search result with respect to a query for the sequence corresponding to the $26^{th}$ to $28^{th}$ base positions of the reference sequence in the subject sequence.

As such, the nucleic acid sequence searching apparatus 1 may correctly and efficiently search the compressed subject sequence, that is, the converted string of characters or encoded codes, directly for desired DNA information, without restoring the compressed subject sequence to its original form.

FIG. 7 is a diagram for explaining the process in the sequence converting unit 104 of converting a search result (converted string of characters) into a sequence, according to an embodiment of the present invention. Referring to FIG. 7, the string of characters 701 corresponding to the $26^{th}$ to $28^{th}$ base sequences of the subject sequence is 'LXL', the sequence converting unit 104 converts the characters found into a base sequence, for the current example, 'A-A,' by reference to the conversion rule, and then outputs the base sequence as the response to the query.

Referring back to FIG. 1, the storage unit 11 stores information processed in the compression unit 101, the index unit 102, and the searching unit 103. In addition, the storage unit 11 also stores the conversion rule and the conversion code of Table 1. As described above, the storage unit 11 stores a string of characters, encoded codes and a compressed subject sequence which are converted by the compression unit 101. In addition, the storage unit 11 also stores an index created by the index unit 102, the result from a query search by the searching unit 103, and the sequence converted by the sequence converting unit 104.

According to the present embodiment, compression of a DNA sequence, creation of an index with respect to the compressed DNA sequence, and search of a DNA sequence may be independently performed. For example, the compression unit 101 only compresses the DNA sequence, however the index unit 102 need not create the index right after the compression process. That is, the compression unit 101, the index unit 102, and the searching unit 103 may independently perform their respective functions in terms of space and time.

Figure 8:
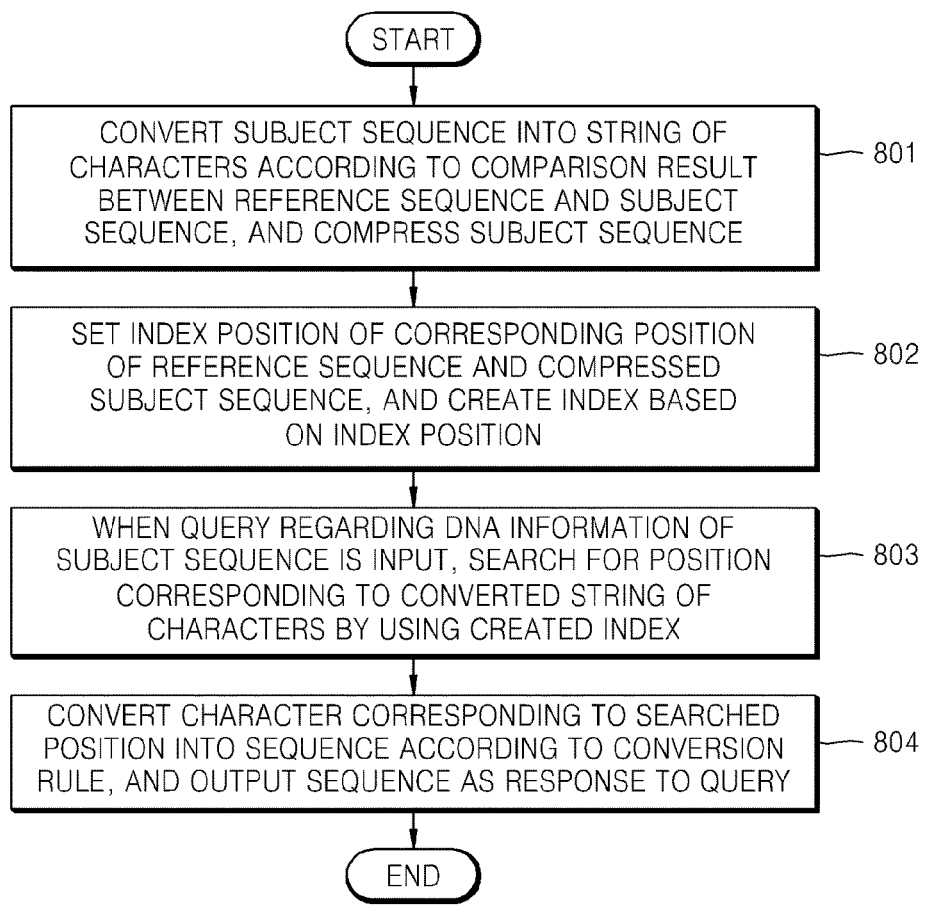
FIG. 8 is a flowchart of a method of searching a nucleic acid sequence, according to an embodiment of the present invention.

FIG. 8 is a flowchart of a method of searching a DNA sequence, according to an embodiment of the present invention. Referring to FIG. 8, the method of searching the DNA sequence includes time-domain operations that are processed in the DNA sequence searching apparatus 1 of FIG. 1. Thus, the description of the DNA sequence searching apparatus 1 of FIG. 1 also applies to the method of searching the DNA sequence according to the present embodiment.

In operation 801, the compression unit 101 compares a reference sequence having known DNA information with a subject sequence to be encoded, converts the subject sequence into a string of characters according to a conversion rule, and compresses the subject sequence by using the converted string of characters.

In operation 802, the index unit 102 sets an index position of a corresponding position of the reference sequence and the compressed subject sequence, and creates an index based on the index position.

In operation 803, when a query regarding DNA information of the subject sequence is input, the searching unit 103 searches for the position corresponding to the converted string of characters by using the created index.

In operation 804, the sequence converting unit 104 converts the character found in the corresponding position into a sequence according to the conversion rule, and outputs the sequence as the response to a query.

Figure 9:
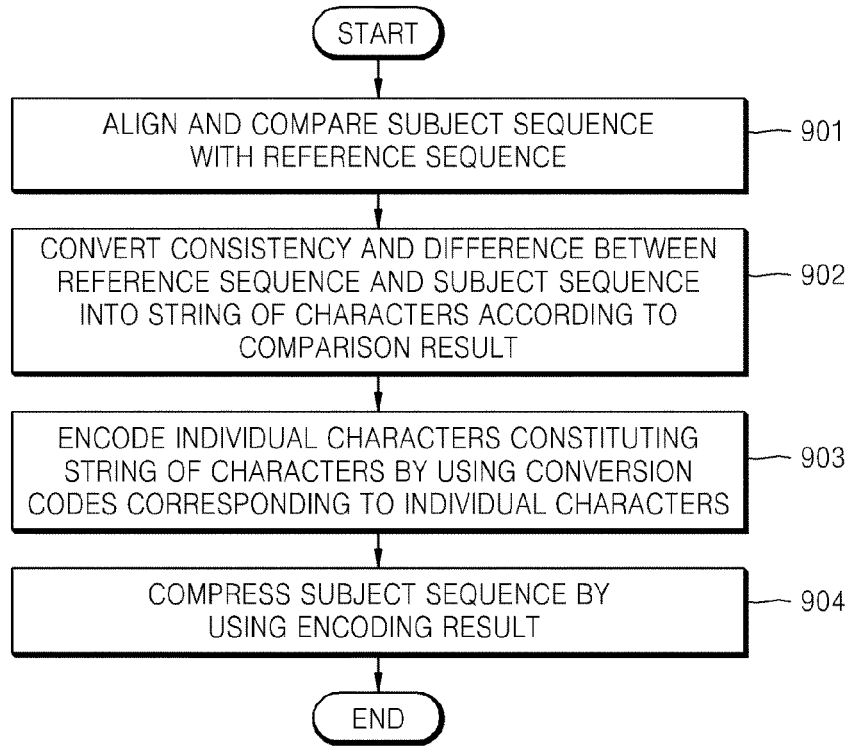
FIG. 9 is a detailed flowchart of the compression operation 801 of FIG. 8.

FIG. 9 is a detailed flowchart of operation 801 of FIG. 8. Operation 801 of FIG. 9 includes time-domain operations performed in the compression unit 101 of FIG. 1.

In operation 901, the comparing unit 1011 aligns and compares a subject sequence with a reference sequence.

In operation 902, the character converting unit 1012 extracts the consistency and difference between the reference sequence and the subject sequence according to the comparison result, and converts the consistency and difference into a string of characters according to the conversion rule.

In operation 903, the encoding unit 1013 encodes individual characters constituting the string of characters by using conversion codes corresponding to the individual characters.

In operation 904, the sequence compressing unit 1014 compresses the subject sequence by using the encoding result based on the conversion codes from the string of characters.

Figure 10:
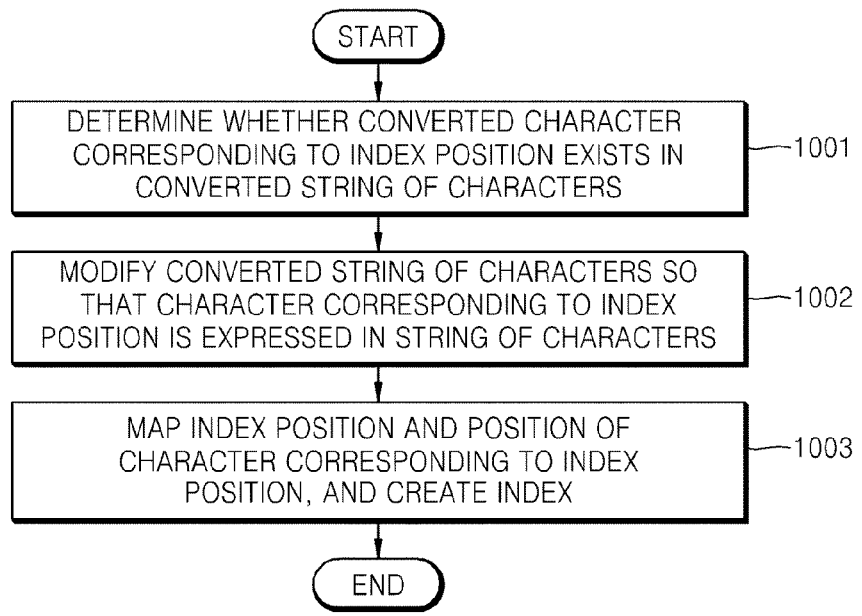
FIG. 10 is a detailed flowchart of the index creation operation 802 of FIG. 8.

FIG. 10 is a detailed flowchart of operation 802 of FIG. 8. Operation 802 of FIG. 10 includes time-domain operations performed in the index unit 102 of FIG. 1.

In operation 1001, the character-string determining unit 1021 determines whether a converted character exists in the converted string of characters in the position of the subject sequence corresponding to the index position.

In operation 1002, when the character-string determining unit 1021 determines that the character at the index position is not explicitly expressed in the converted string of characters, the character-string modifying unit 1022 modifies the converted string of characters so that the converted character at the position of the subject sequence corresponding to the index position is expressed in the string of characters.

In operation 1003, the index creating unit 1023 maps the index position and the position of the character corresponding to the index position in the converted string of the character, and creates an index.

Figure 11:
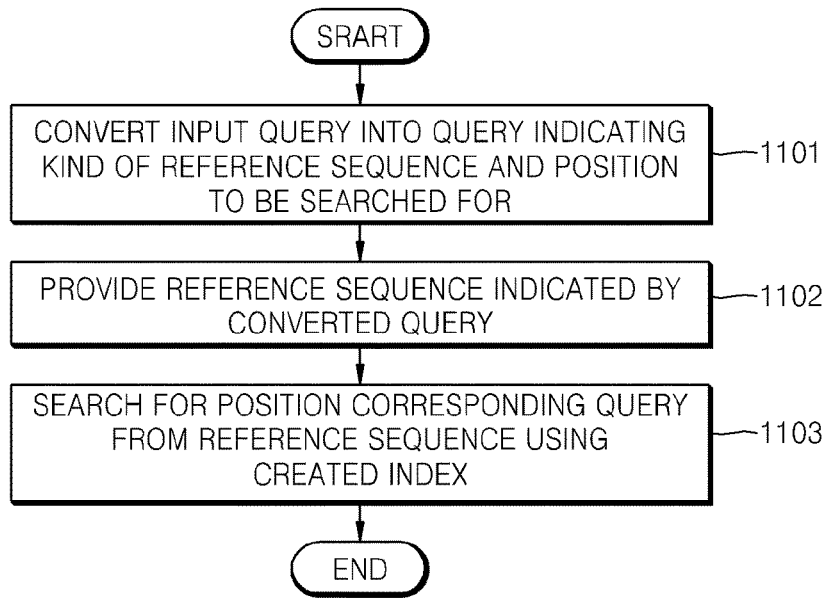
FIG. 11 is a detailed flowchart of the searching operation 803 of FIG. 8.

FIG. 11 is a detailed flowchart of operation 803 of FIG. 8. Operation 803 of FIG. 11 includes time-domain operations performed in the searching unit 103 of FIG. 1.

In operation 1101, the query converting unit 1031 converts an input query into a query indicating the kind of reference sequence (i.e., a particular gene or a chromosome, and/or an organism), and a position to be searched for in a subject sequence.

In operation 1102, the sequence providing unit 1032 provides the reference sequence requested by the converted internal query.

In operation 1103, the sequence searching unit 1033 searches for the position corresponding to the query in the converted string of characters representing the compressed subject sequence using the created index to locate index positions near the query position.

Figure 12:
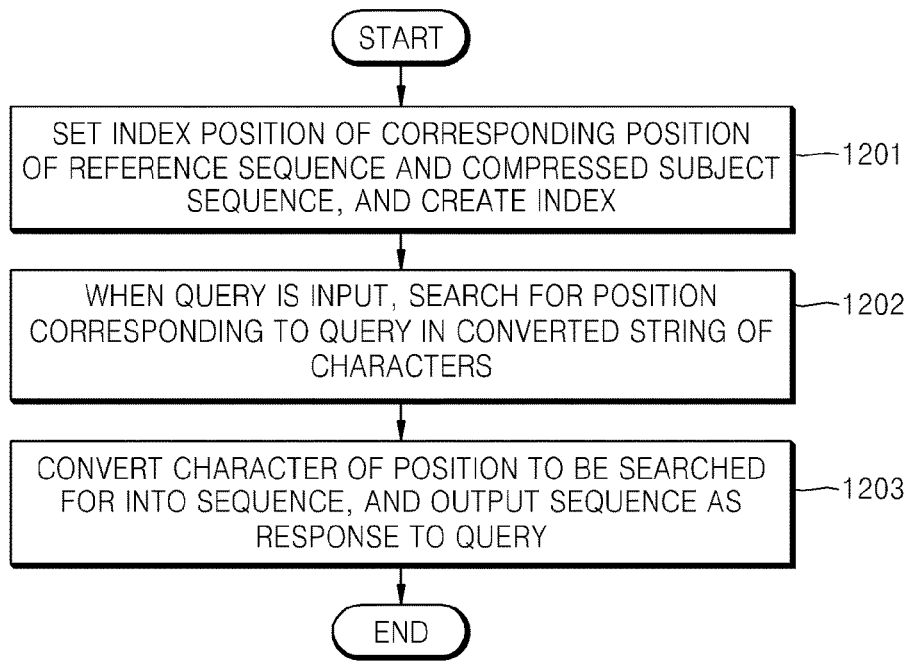
FIG. 12 is a flowchart of a method of searching a DNA sequence, according to another embodiment of the present invention.

FIG. 12 is a flowchart of a method of searching a DNA sequence, according to another embodiment of the present invention. Referring to FIG. 12, the method of searching the DNA sequence includes time-domain operations that are processed in the DNA sequence searching apparatus 1 of FIG. 1. Thus, the description of the DNA sequence searching apparatus 1 of FIG. 1 also applies to the method of searching the DNA sequence according to the present embodiment.

In operation 1201, the index unit 102 sets an index position for a position of the reference sequence corresponding to a position in the compressed subject sequence, and creates an index based on the index position.

In operation 1202, when a query regarding DNA information of a subject sequence is input, the searching unit 103 searches for the position corresponding to the query in the converted string of characters by using the created index.

In operation 1203, the sequence converting unit 104 converts the character found at the position into a sequence according to the conversion rule, and outputs the sequence as the response to the query.

The embodiments of the present invention can be written as computer programs and can be implemented in specific- or general-use computers that execute the computer programs stored on a non-transitory computer readable recording medium. Data used in the above-described embodiments can be recorded on the non-transitory computer readable recording medium in various ways. Non-limiting examples of the non-transitory computer readable recording medium are magnetic storage media, such as read only memory ("ROM"), floppy disks and hard disks, for example, as well as optical recording media, such as compact disc-ROMs ("CD-ROMs") or digital versatile discs ("DVDs"), for example, but are not limited thereto.

As described above, according to the one or more of the above embodiments of the present invention, a nucleic acid sequence of an organism may be compressed at a high efficiency without loss of information, and thus efficiency of data storing and data transferring may be increased. In addition, when a nucleic acid sequence is analyzed, the desired information may be correctly searched for in the compressed nucleic acid sequence without restoring the compressed sequence to its original format.

It will be understood that the embodiments described herein will be considered in a descriptive sense only and not for purposes of limitation. Descriptions of aspects within each embodiment should be considered as available for other similar aspects in other embodiments.

While the general inventive concept disclosed herein has been particularly shown and described with reference to exemplary embodiments thereof, it will be understood by those of ordinary skill in the art that various changes in form and details may be made therein without departing from the spirit or scope of the present invention as defined by the following claims.

What is claimed is:

1. A method of searching a nucleic acid sequence, the method comprising:
   comparing a reference nucleic acid sequence with a subject nucleic acid sequence to be encoded, converting the subject sequence into a string of characters according to a conversion rule, and compressing the subject sequence by using the converted string of characters;
   setting an index position of a position of the reference sequence corresponding to a position in the compressed subject sequence, and creating an index correlating reference sequence index position with compressed subject sequence position;
   receiving an input query regarding DNA information at a position of the subject sequence, and searching for the position in the converted string of characters by using the created index; and
   converting a character found at the position into a sequence according to the conversion rule, and outputting the sequence as a response to the query;
   wherein the method is performed by at least one processor.

2. The method of claim 1, wherein creating an index comprises
   mapping an index position that is set with respect to the reference sequence, and a position of a character corresponding to the index position in the converted string of characters of the subject sequence to create an index.

3. The method of claim 2, wherein creating an index comprises:
   determining whether the converted string of characters of the subject sequence has a character at a position in the converted string corresponding to the index position of the reference sequence;
   if the position in the converted string of characters corresponding to the index position does not have a character in the converted string of characters, modifying the converted string of characters so that the position in the converted string corresponding to the index position has a character in the string of characters; and
   mapping the index position and the position of the character corresponding to the index position in the modified string of characters to create an index.

4. The method of claim 1, wherein index positions are set at predetermined intervals in the reference sequence.

5. The method of claim 1, wherein searching for the position comprises
   selecting an index position that is the closest to the position to be searched for from among index positions included in the created index; and
   searching for the position starting from the selected index position.

6. The method of claim 1, wherein searching for the position comprises:
   converting the input query into a query indicating a kind of reference sequence, and a position to be searched for in the reference sequence;
   providing a reference sequence indicated by the converted query; and searching for the position in the reference sequence indicated by the converted query in the converted string of characters of the compressed subject sequence by using the created index.

7. The method of claim 1, wherein, when the received input query is a query regarding a plurality of subject sequences, searching of the position comprises parallely searching for the subject sequences indicated by the converted query.

8. The method of claim 1, further comprising mapping and storing the compressed subject sequence and the created index.

9. The method of claim 1, wherein compressing the subject sequence comprises:
   aligning and comparing the subject sequence with the reference sequence;
   extracting a consistency and a difference between the reference sequence and the subject sequence determined by aligning and comparing the sequences, and converting the consistency and the difference into a string of characters according to the conversion rule;
   encoding individual characters constituting the string of characters by using conversion codes corresponding to the individual characters to obtain a compressed subject sequence,
   wherein the conversion rule indicates that characters are assigned to represent the consistency, the difference, and the number of characters in the consistency or difference, and
   wherein the conversion code indicates that 4-bit and 8-bit codes are assigned to represent the assigned characters.

10. A method of compressing a nucleic acid sequence, the method comprising:
    comparing a reference nucleic acid sequence with a subject nucleic acid sequence to be encoded,
    converting the subject sequence into a string of characters according to a conversion rule,
    compressing the subject sequence by using the converted string of characters to represent the subject sequence;
    setting an index position of a position of the reference sequence corresponding to a position in the compressed subject sequence, and
    creating an index correlating reference sequence position with compressed subject sequence position,
    wherein the method is performed by at least one processor.

11. A method of searching for a nucleic acid sequence in a subject sequence that is compressed from a reference sequence into a string of characters, the method comprising:
    setting an index position of the reference sequence corresponding to a position of the compressed subject sequence, and creating an index;
    receiving a query regarding information at a position of the subject sequence,
    searching for the position corresponding to the query in the converted string of characters of the compressed subject sequence using the created index;
    converting a character found in the position of the converted string of characters into a sequence according to a conversion rule used to compress the subject sequence, and outputting the sequence as a response to the query;
wherein the method is performed by at least one processor.

12. A nontransitory computer readable recording medium having recorded thereon a program for executing the method of claim 1.

13. A nontransitory computer readable recording medium having recorded thereon a program for executing the method of claim 10.

14. A nontransitory computer readable recording medium having recorded thereon a program for executing the method of claim 11.

15. An apparatus for searching a nucleic acid sequence, the apparatus comprising:
a processor comprising:
a compression unit for comparing a reference sequence with a subject sequence to be encoded, converting the subject sequence into a string of characters according to a conversion rule, and compressing the subject sequence by using the converted string of characters;
an index unit for setting an index position of a position of the reference sequence corresponding to a position of the compressed subject sequence, and creating an index correlating the index position with the compressed subject sequence position;
a searching unit, for searching for a position in a subject sequence requested by an input query in the converted string of characters representing the subject sequence by using the created index; and
a sequence converting unit for converting a character found at a position in a string of characters representing a subject sequence into a sequence according to the conversion rule, and outputting the sequence as a response to an input query.

16. The apparatus of claim 15, wherein the index unit comprises:
a character-string determining unit for determining whether a converted character exists at a position in the converted string of characters of the subject sequence corresponding to the index position;
a character-string modifying unit, for modifying the converted string of characters when a character is not present in the converted string of characters at a position corresponding to the index position so that a character is present in the converted string of characters at the position corresponding to the index position; and
an index creating unit for mapping the index position and a position of the character corresponding to the index position in the modified string of characters, and creating an index.

17. The apparatus of claim 15, wherein the searching unit comprises:
a query converting unit for converting an input query into a query indicating a kind of reference sequence, and a position of the reference sequence to be searched for in the subject sequence;
a sequence providing unit for providing a reference sequence indicated by a converted query; and
a sequence searching unit for searching for a position indicated by a converted query in a converted string of characters of the subject reference sequence by using the created index.

18. The apparatus of claim 15, wherein, when the input query is a query regarding a plurality of subject sequences, the searching unit parallely searches for the subject sequences indicated by the converted query.

19. The apparatus of claim 15, further comprising a storage unit for mapping and storing the reference sequence, the subject sequence that is compressed by using the reference sequence, and the created index.

20. The apparatus of claim 15, wherein the compression unit comprises:
a comparing unit for aligning and comparing the subject sequence with the reference sequence;
a character converting unit for extracting a consistency and difference between the reference sequence and the subject sequence determined by the aligning and comparing, and converting the consistency and the difference into a string of characters according to the conversion rule;
an encoding unit for encoding individual characters constituting the string of characters by using conversion codes corresponding to the individual characters; and
a sequence compressing unit for compressing the subject sequence by using the encoded string of characters,
wherein the conversion rule indicates characters are assigned to represent the consistency, the difference, and the number of characters in the consistency or difference between the reference sequence and the subject sequence, and
wherein the conversion code indicates that 4-bit and 8-bit codes are assigned to represent the assigned characters.

21. An apparatus for searching a nucleic acid sequence in a subject sequence that is converted from a reference sequence into a string of characters, the apparatus comprising:
a processor comprising:
an index unit for setting as an index position a position of the reference sequence corresponding to a position of the compressed subject sequence, and creating an index correlating the index position with the compressed subject sequence position;
a searching unit, for searching for a position in the subject sequence requested by an input query in the converted string of characters representing the subject sequence by using the created index; and
a sequence converting unit for converting a character found character at a position in a string of characters representing a subject sequence into a sequence according to the conversion rule, and outputting the sequence as a response to an input query.

* * * * *

SEQUENCE LISTING

<160> NUMBER OF SEQ ID NOS: 2

<210> SEQ ID NO 1
<211> LENGTH: 46
<212> TYPE: DNA
<213> ORGANISM: Artificial Sequence
<220> FEATURE:
<223> OTHER INFORMATION: Reference construct

<400> SEQUENCE: 1
gcttcactaa tgcaagtaga aaaacaaat aagtgttatg aatccc           46

<210> SEQ ID NO 2
<211> LENGTH: 46
<212> TYPE: DNA
<213> ORGANISM: Artificial Sequence

```
<220> FEATURE:
<223> OTHER INFORMATION: Personal Genome construct

<400> SEQUENCE: 2
gcttgactaa tgcaagtaga aaaataaaat aagtgttatg aatccc                46
```